(12) United States Patent
Stössel et al.

(10) Patent No.: US 7,250,519 B2
(45) Date of Patent: Jul. 31, 2007

(54) METHOD FOR THE PRODUCTION OF ARYLAMINES

(75) Inventors: Philipp Stössel, Frankfurt (DE); Hubert Spreitzer, Viernheim (DE); Heinrich Becker, Eppstein-Niederjosbach (DE)

(73) Assignee: Merck Patent GmbH, Darmstadt (DE)

( * ) Notice: Subject to any disclaimer, the term of this patent is extended or adjusted under 35 U.S.C. 154(b) by 251 days.

(21) Appl. No.: 10/494,081

(22) PCT Filed: Oct. 25, 2002

(86) PCT No.: PCT/EP02/11942

§ 371 (c)(1), (2), (4) Date: Oct. 29, 2004

(87) PCT Pub. No.: WO03/037844

PCT Pub. Date: May 8, 2003

(65) Prior Publication Data

US 2005/0054854 A1    Mar. 10, 2005

(30) Foreign Application Priority Data

Oct. 30, 2001  (DE) ................................ 101 53 450

(51) Int. Cl.
*C07D 211/05* (2006.01)
*C07D 43/02* (2006.01)
*C07D 29/10* (2006.01)

(52) U.S. Cl. ...................... 546/404; 546/208; 546/203; 546/205; 548/577; 548/517

(58) Field of Classification Search ................ 546/208, 546/203, 205, 404; 548/577, 517
See application file for complete search history.

(56) References Cited

U.S. PATENT DOCUMENTS 6,476,265 B1    11/2002   Spreitzer et al.

FOREIGN PATENT DOCUMENTS

| DE | 35 21 770 A1 | 1/1986 |
| DE | 100 02 561 A1 | 7/2001 |
| EP | 0 802 173 B1 | 10/1997 |
| JP | 11 322679 | 11/1999 |
| JP | 2000007689 | 1/2000 |
| WO | WO 99/12888 | 3/1999 |
| WO | WO 01/40147 | 6/2001 |

*Primary Examiner*—Samuel Barts
(74) *Attorney, Agent, or Firm*—Hamilton, Brook, Smith & Reynolds, P.C.

(57) ABSTRACT

The invention relates to a method for the production of tertiary amines by reaction of secondary amines with aromatics or heteroaromatics in the presence of a base, a nickel or palladium compound and one or several phosphines, dialkoxy-, and/or diaryloxyphosphines in an inert solvent.

Aromatic or heteroaromatics of this type play an important role in industry as reagents or intermediates for pharmaceuticals and agrochemicals and in diverse fine and electronics chemicals, above all in the rapidly growing field of organic semi-conductors, in particular in organic or polymeric light diodes, organic solar cells and organic ICs.

25 Claims, No Drawings

METHOD FOR THE PRODUCTION OF ARYLAMINES

RELATED APPLICATIONS

This application is the U.S. National Stage of International Application No. PCT/EP02/11942, filed Oct. 25, 2002, published in German, and claims priority under 35 U.S.C. § 119 or 365 to German Application No. 101 53 450.7, filed Oct. 30, 2001.

Aromatic or heteroaromatic amines play a significant role in industry as, for example, reagents or intermediates for pharmaceutical or agrochemical products and in diverse applications in the fields of fine chemistry and electronics chemicals to mention but a few. Above all else, these compounds are of outstanding importance in the strongly growing field of organic semi-conductors (e.g. for applications in organic or polymeric light diodes, organic solar cells, organic ICs).

Different alternative methods are known for their preparation but in some cases these are neither economic nor capable of offering an ecologically satisfactory solution.

The method employing a direct linking between an amine and an arylhalide in a so-called C—N-coupling reaction is frequently employed (see Scheme 1)

scheme 1. General reaction equation for a C-N-coupling reaction

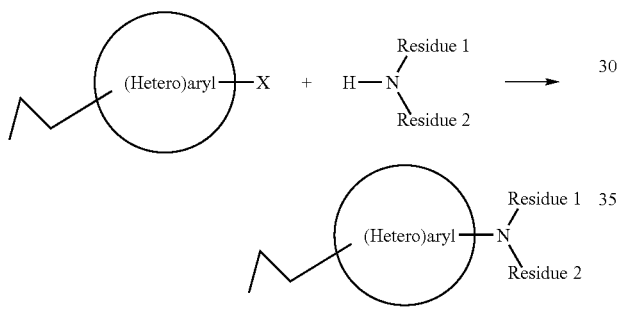

Although this reaction has already been the subject of research for a number of years, there is still a lack of a practical industrial procedure. The first efforts in this direction were made by the work group of Buchwald et al, the Tosoh Co. and the Du Pont de Nemours Company. These studies (see U.S. Pat. No. 5,576,460, EP-A-0 802 173 and WO 01/40147) represent the latest state of the technology prior to this application and they are hereby regarded by way of a citation as a component part of this application. This is in order to avoid repeating the detailed descriptions given therein relating to the general state of the technology with respect to amination- or C—N-coupling reactions. In U.S. Pat. No. 5,576,460 Buchwald et al were able to show that secondary or tertiary amines are obtained by reacting an appropriate halo-aromatic or haloheteroaromatic with an appropriate primary or secondary amine in the presence of a base, a palladium compound and, optionally, a tertiary phosphine in a solvent. In this way and under conditions which are compatible with industrial practice conversion grades of up to 90% can be obtained.

In the application WO 01/40147 it could be shown that C—N-couplings are also catalysed by phosphine oxides of secondary phosphines having the general formula $H(O)PR_2$. The phosphineoxide can be used as such in the process or it can be introduced—before the addition of the reacting substances—by the hydrolysis with water of a corresponding readily-hydrolysable phosphineoxide precursor. Conversion rates of up to 67% are described for the reaction of chloro-aromatics with primary alkyl- and arylamines or with secondary alkylamines, without any reference being made to the coupling of halo-aromatics and, in particular, bromo-aromatics with diarylamines (see also Table I, Experimental Section in WO 01/40147).

In EP-A-0 802 173 it could be shown that the coupling of secondary amines with appropriate halo-aromatics or halo-heteroaromatics accompanied by the use of tertiary phosphines, especially trialkylphosphines with a large cone angle (Tolman-Angle) leads to still better results. If the trialkylphosphine with a large cone angle is used, e.g. tri-tert-butylphosphine technically acceptable conversion rates of up to 97% are achieved (see, in particular, Example 14, 20–24, 34, 40 and 47 in EP-A-0 802 173).

The conditions described and published in EP-A-802 173 are adequate for the development of many simple conversions to achieve economically acceptable procedures. However, a problem arises with the representation of a multifunctional compound. In the context of this application, the term multi-functional is meant to signify that a compound contains several (i.e. two, three, four, five, etc.) identical or similar functional units (centres), all of which react in the corresponding conversion process to produce a product molecule. The conversion of multi-functional compounds is intended to represent in the first place the reaction of a multifunctional compound with several monofunctional compounds to form a defined "low-molecular" compound. (see Scheme 2)

scheme 2

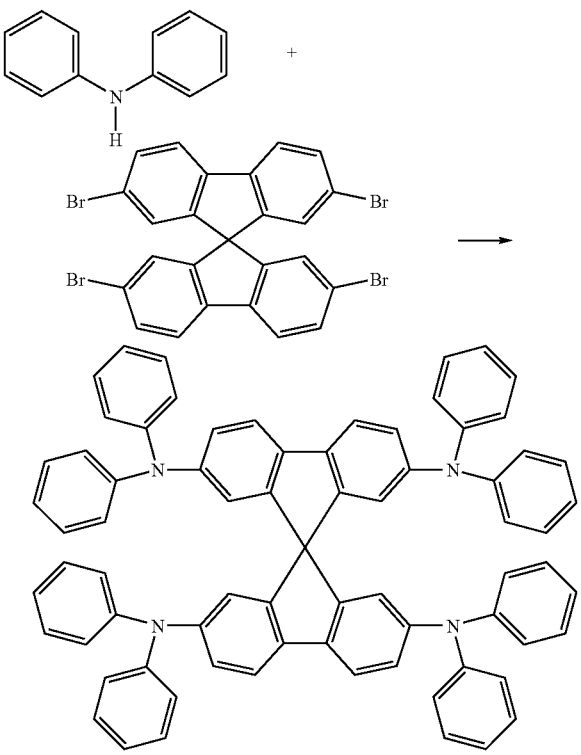

Example of the reaction of a multifunctional compound (4 centres).

In the representation of multi-functional compounds conversion grades of even up to 99% with regio-selectivities of up to 99% can lead to distinct problems.

Variations from the above-mentioned regio-chemistry of the coupling activity are typical side-reactions of the named procedure. They result from the fact that the C—N-link just made does not take up the position which was previously occupied by the halogen atoms of the halo-aromatics or the haloheteroaromatics, but rather that the newly-formed C—N link is displaced by one position (see Scheme 3).

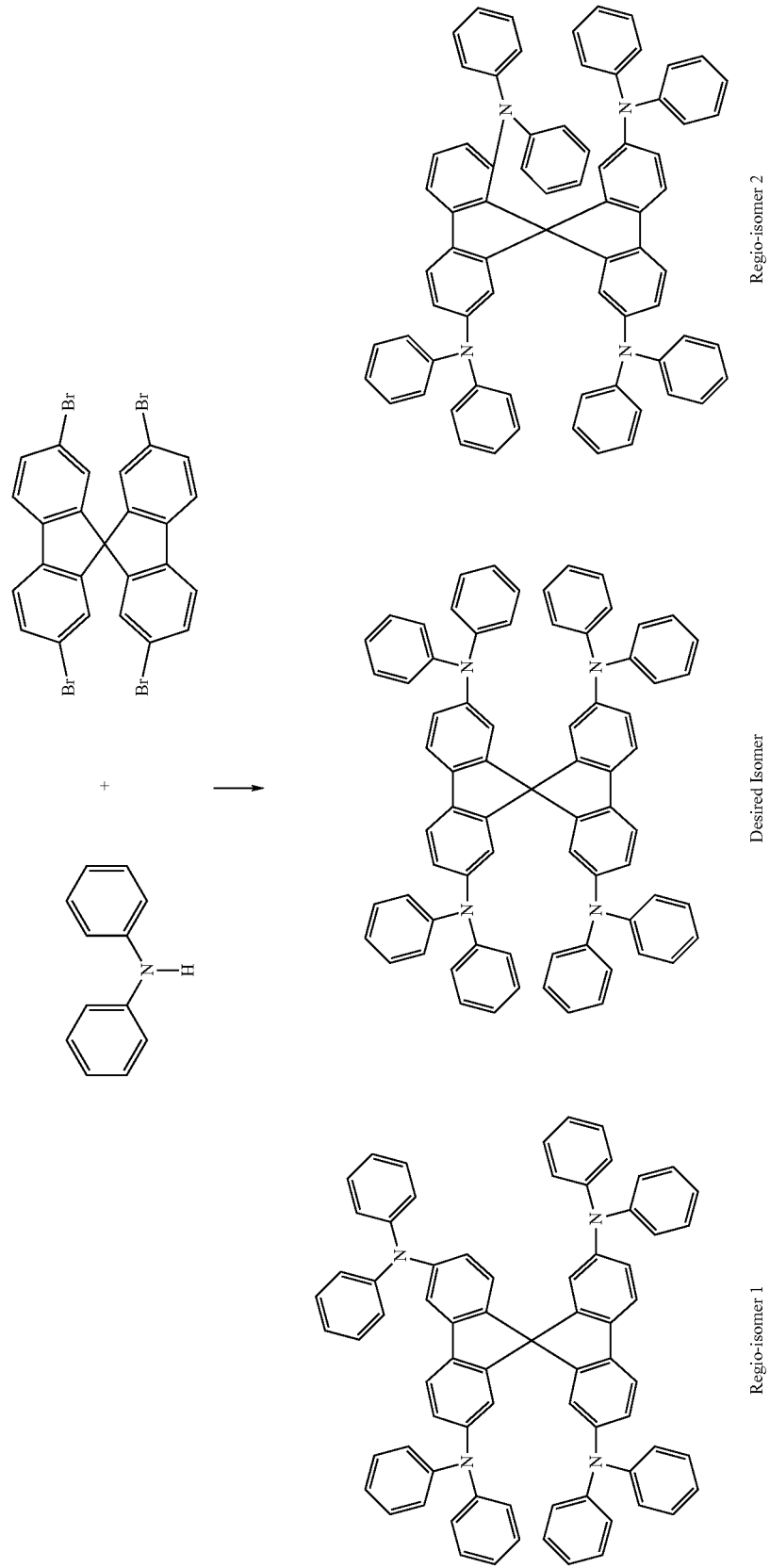

Thus as shown in Schemes 2 and 3, a typical conversion rate (per single stage) of 99% with a typical regio-selectivity of an assumed 99% (i.e. for each individual addition, 0.99× 0.99=98% yield of the desired substitution product) results in an overall yield of about 92%. Experience shows that the conversion rates specified in the above examples of up to 99% for regio-selectivities of up to 99% when using the procedure described in the U.S. Pat. No. 5,576,460 and EP-A-0 802 173 are singular instances which can be attained in practice only in the case of certain selected substrates, in particular those in which the formation of regio-isomers is suppressed by stereometric group congestion. (see example 47 in EP-A-0 802 173).

However, in view of the purity requirements of +99.9% in, for example, electronic applications the relatively high yield is still unsatisfactory since the purification procedure is extensive on account of the high number of different byproducts and especially the regio-isomers which exhibit a very similar crystallisation behaviour to that of the desired isomer, and itself strongly reduces the final yield level (see Table 1 of this Description). The above-mentioned example clearly shows that the use of the named procedures for the synthesis of highly-purified, multi-functional compounds is inadequate.

A disadvantage of the tertiary phosphines used in the catalyst systems according to EP-A-0 802 173 is their marked sensitivity to air which, in the case of tri-tert-butylphosphine is so pronounced that when this phosphine is exposed to air spontaneous combustion can occur. Especially in the case of technical applications, very special precautions have to taken when using this compound, which—in addition to the natural high price of this compound—militates against its use on a larger scale.

Based on what has been said above, it is clear that the indicated C—N-coupling procedures are on the one hand satisfactory in principle for representing appropriate arylamines but, on the other hand the methods employed so far are still inadequate for certain requirements (multiple reaction centres, multi-functional). Consequently, there is a clear need for an improvement in the state of the technology described above.

Surprisingly, it has now been found that C—N-coupling reactions described above as representing the state of the technology can be improved decisively by a clearly defined modification with the result that the above-mentioned problems can be resolved.

The new procedure according to the invention describes a method for the preparation of tertiary amines of the formula (I)

by reacting secondary amines of the formula (II)

with aromatics or heteroaromatics of the formula (III)

in the presence of a base and a nickel or palladium compound and one or more phosphine(s) selected from the group of monomeric, oligomeric and/or polymeric halo-phosphines of the general formula Y—PR4R5, dihalo-phosphines of the general formula (Y)$_2$PR4, alkoxy- and/or aryloxy-phosphines of the general formula R3O—PR4PR5, dialkoxy- and/or diaryloxy-phosphines of the general formula (R3O)$_2$—PR4 as well as mixtures of these with one another in an inert solvent.

Aromatics- or heteroaromatics (X)$_n$—Ar in the context of this application are aromatics having 6 to 40 C-atoms and/or heteroaromatics with 2 to 40 C-atoms, either of which can be substituted or unsubstituted by one or more linear, branched or cyclic alkyl- or alkoxy residues having 1 to 20 C-atoms where again one or more non-vicinal CH$_2$-groups may be replaced by O, S, C═—O, or a carboxy group; or by unsubstituted C-4 to C-20 aryl- or heteroaryl residues, fluorine or cyano- or nitro-groups. Compounds which can be used with preference are the corresponding substitute or unsubstituted derivatives of benzol, naphthalene, anthracene, pyrene, biphenyl, fluorene, spiro-9,9'-bifluorene, phenanthrene, triptycene, pyridine, furan, thiophene, pyrolle, quinolene, quinoxaline, pyrimidine and pyrazine.

Monofunctional aromatics are distinguished by n=1, polyfunctional aromatics by n>1 with n preferably less than or equal to 10. Preferably n stands for a whole number 1, 2, 3, 4, 5, 6, 7, 8, 9 or 10 with a particular preference for one of the whole numbers 1, 2, 3, 4, 5 or 6.

The functional group X in the aryl- or heteroaryl compound is a suitable reactive leaving group suitable for the described reaction. Preferably this is chlorine, bromine, iodine, methylsulphonate, tosylate, triflate, nonaflate or a diazonium salt grouping.

In the case of the secondary amines of the type H—NR1R2 used in accordance with the invention on every occasion the residues R1 and R2 are the same or different and stand for a linear, branched mono- bi-, tri- or poly-cyclic aliphatic with 1 to 20 C-atoms where the nitrogen may form a part of the ring system and where again one or more non-vicinal CH$_2$-groups may be substituted by NR4, O, S, C═O or a carboxy-group, and aromatics with 6 to 40 C-atoms or heteroaromatics with 2 to 40 C-atoms, either of which can be unsubstituted or substituted by one or more linear, branched or cyclic alkyl- or alkoxy residues having 1 to 20 C-atoms where again one or more non-vicinal CH$_2$-groups may be replaced by O, S, C═—O, or a carboxy group; or by unsubstituted C-4 to C-20 aryl- or heteroaryl residues, fluorine or cyano- or nitro groups.

Preferred alkyl residues for R1 and R2 are methyl-, ethyl-, propyl-, iso-propyl-, butyl, iso-butyl, sec-butyl-, tert-butyl-, cyclopentyl-, cyclohexyl-, cycloheptyl-, N-methylpiperazinyl- and morpholino residues.

Preferred aryl- or heteroaryl residues with respect to R1 and R2 are the corresponding substituted or unsubstituted derivatives of benzol, naphthalene, anthracene, pyrene, biphenyl, fluorene, spiro-9-9'-bifluorene, phenanthrene, triptycene, pyridine, furan, thiophene, pyrrole, quinoline, quinoxaline, pyrimidine and pyrazine.

The bases are used in an analogous manner to those in the applications for U.S. Pat. No. 5,576,460 and EP-A-0 802 173. Those used may include both inorganic bases, especially alkali- and alkaline earth metal carboxylates, -carbonates, -hydrogen carbonates and -phosphates such as sodium and potassium acetate, -carbonate and -phosphate as well as organic bases, especially metal alcoholates of the type MO—R3, where M is an electropositive metal, preferably, lithium, sodium, potassium, magnesium and zinc and R3 is a simple linear or branched alkyl residue with 1 to 12 C-atoms, preferably methyl-, ethyl-, propyl-, iso-propyl-, butyl-, sec-butyl-, iso-butyl-, tert-butyl-, tert-pentyl-, tert-hexyl- or a simple aryl residue having 6 to 12 C-atoms which is preferably phenyl. It may be preferred to use oligomeric or polymeric metal-alcoholates where, in this case R3 corresponds to an oligomeric or polymeric alcohol, in which cases R3 represents an oligomeric or polymeric alcohol in the broadest sense.

The use of the metal alcoholate sodium-tert-butanolate as the base is given special preference. Optionally, mixtures of the bases may be used. In the case of the monomeric, oligomeric and/or polymeric phosphine used, these are one or more compounds selected from the group of halo-phosphines of the type Y—PR4R5, di-halo-phosphines of the type (Y)$_2$—PR4 alkoxy- and/or aryloxy-phosphines of the type R3O—PR4R5, dialkoxy- and/or diaryloxy-phosphines of the type (R3O)$_2$—PR4, as well as mixtures of these.

In each case, the residues R4 and R5 are the same or different and stand for a linear, branched or mono-, di- or tricyclic alkyl-residue with 1 to 12 C-atoms, where again one or more non-vicinal CH$_2$-groups may be substituted by O, or an aryl or heteroaryl-residue with 4 to 12 C-atoms which can be substituted by one or more linear, branched or cyclic alkyl- or alkoxy residues with 1 to 10 C-atoms, where again one or more non-vicinal CH$_2$-groups can be substituted by O, S, C═O or a carboxy group.

Preferred alkyl residues for R4 and R5 are methyl-, ethyl-, propyl-, iso-propyl-, butyl-, iso-butyl-, sec-butyl-, tert-butyl-, tert-pentyl-, tert-hexyl-, cyclopentyl-, cyclohexyl-residues.

Preferred aryl- or heteroaryl residues with respect to R4 and R5 are the phenyl-, o-tolyl-, 2,6-dimethylphenyl, mesityl-, 2-iso-propylphenyl-, 2,6-di-iso-propylphenyl-, 2-tert-butylphenyl-, 2-methoxyphenyl-, 2,6-dimethoxyphenyl-, 2,4,6-trimethoxyphenyl- and 2-biphenyl-residues.

Instead of the above-described monomeric halo-, dihalo-, alkoxy, aryloxy-, dialkoxy- and/or diaryloxy phosphines, there can be a preference for the use of oligomeric or polymeric supported halo-, dihalo-, alkoxy-, aryloxy, dialkoxy- and/or diaryloxy-phosphines corresponding to Scheme 4, where in these instances the residues R4 and/or R5 can be an oligomeric or polymeric matrix in the broadest sense.

Instead of the above-described monomeric alkoxy-, aryloxy, dialkoxy-, and/or diaryloxy phosphines there may also be a preference for the use of oligomeric or polymeric supported alkoxy-, aryloxy-, dialkoxy- and/or diaryloxy phosphines in accordance with Scheme 5, where in these instances, R3 corresponds to an oligomeric or polymeric alcohol in the broadest sense.

The group Y stands for halogen, preferably chlorine or bromine.

The procedure described here is characterised in that a halo-phosphine of the type Y—PR4R5 or a di-halo-phosphine of the type Y$_2$—PR4 can be used as the phosphine in question but, as mentioned above, it is not restricted to this example.

Under the reaction conditions, the halo-phosphines or the dihalo-phosphines undergo, possibly in situ, a conversion to alkoxy-, aryloxy, dialkoxy- or diaryloxy phosphines via a salt-metathetic reaction with the added base (metal-alcoholate, MO—R3), in accordance with Scheme 6:

Scheme 6:
Possible salt-metathetic reaction of the halo-phosphines with the bases

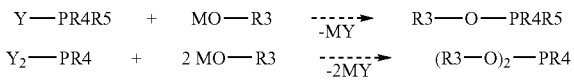

Such alkoxy-, aryloxy-, dialkoxy- or diaryloxy-phosphines are equally in accordance with the invention and a constituent of the Description regardless of whether they are formed in situ in the reaction mixture or they are previously formed by reaction of a halo-phosphine of the type Y—PR4R5 or a dihalo-phosphine of the type Y$_2$—PR4 with a metal alcoholate MO3—R3 and then added to the reaction mixture or they are added as a pure material.

As the halo-phosphines, preference is given to the use of chloro-di(iso-propyl)phosphine, chloro-di(iso-butyl)phosphine, chloro-di(tert-butyl)phosphine, chloro-di(cyclohexyl)phosphine, chloro-di(o-tolyl)phosphine, chloro-di(mesityl)phosphine, chloro-bis(2-methoxyphenyl)phosphine, chloro-bis(2,4,6-trimethoxyphenyl)phosphine or the analogous/derived alkoxy- or aryloxy-phosphines and as the dihalo-phosphines preference is given to the use of dichloro-isopropylphosphine, dichloro-iso-butylphosphine, dichloro-tert-butylphosphine, dichlorocyclohexylphosphine, dichloro-o-tolylphosphine, dichloro-mesitylphosphine, dichloro-2-methoxyphenylphosphine, dichloro-2,4,6-trimethoxyphenylphosphine or the analogous /derived dialkoxy- or diaryl phosphines. Specially preferred halo-phosphines are chloro-di(iso-propyl)phosphine, chloro-di(tert-butyl)phosphine and chloro-bis(2,4,6-trimethoxyphenyl) phosphine or the analogous/derived alkoxy- or aryloxy phosphines and the specially preferred dihalo-phosphines are dichloro-iso-propylphosphine, dichloro-tert-butylphosphine, dichloro-2,4,6-trimethoxyphenyl phosphine or the analogous/derived dialkoxy- or diaryloxy-phosphines.

The nickel compound in accordance with the invention is a nickel (II) compound preferably nickel-(II)halogenides, nickel-(II)-biscarboxylates, nickel-(II)-ketonates or complexes derived therefrom such as such as olefinenickel-(II)halogenides, allylnickel-(II)-halogenides or also dispersed or colloidal metal nickel supported or not supported or also other nickel-(II)-compounds. The palladium compound in accordance with the invention is that of a palladium-(II)-compound, preferably palladium-(II)-halogenides, palladium-(II)-biscarboxylates, palladium-(II)-ketonates or simple complexes derivable therefrom such as nitrilepalladium-(II)-halogenides, olefine-palladium-(II)-halogenides, allyl-palladium-(II)-halogenides or also dispersed or colloidal metallic palladium supported or not supported or other palladium-(0) compounds. Special preference is given to the use of palladium-(II)-acetate or tris-(dibenzylideneacetone)-dipalladium (0) (Pd$_2$(dba)$_3$ or Pd$_2$(dba)$_3$×CHCl$_3$ as the palladium compound.

Inert solvents are used as the solvent, i.e. with a preference for aprotic solvents, particularly aromatic solvents such as toluol, the isomeric xylols or mixtures of these, ethers, cyclic ethers and polyethers such as di-iso-propylether, methyl-tert-butylether, di-n-butylether, anisole, tetrahydrofurane, dioxane, di-, tri- and tetra-ethyleneglycoldimethyl- or ethylethers and oligo- or polyethyleneglycol- or ethylethers, NN-dialkylcarboxylicacidamides and N-alkyllactones such as dimethylformamide, dimethylacetamide or N-methylpyrrolidine-2-one. It is also possible to use mixtures of these solvents.

In the procedure in accordance with the invention the nickel- or palladium compound is normally used at a rate of 0.00001 ml % to 10 mol % (nickel or palladium), with respect to the quantity of C—N-coupling points which are to be closed. Preferably, the range used here is between 0.001 to 5%, with a special preference for the range between 0.01–2.5%.

In the case of the procedure in accordance with the invention the molecular ratio of the nickel- or palladium compound to the halo-phosphine having the general formula Y—PR4R5, to the dihalo-phosphine of the general formula Y₂PR4, to the alkoxy- or aryloxy phosphine of the general formula R3O—PR4R5 or to the dialkoxy- or diaryloxy-phosphine of the general formula (R3O)₂—PR4 lies between 0.5 and 20 with a preference for between 1 and 8. As a rule, the base, especially the metal alcoholate M—OR3 is added in a ratio of between 0.5 and 10 equivalents with respect to the C—N— linkage points to be closed. Preferably, the range here is between 0.8 and 5 equivalents with a special preference for between 1.0 and 3 equivalents.

The concentration of the reactands in the solvent depends naturally upon the special reaction involved. There is a preference, however, for the reaction to take place within a range of between 0.1 mol/l and 5 mol/l with respect to the quantity of C—N-linkages to be closed.

The reaction in accordance with the invention is thermally activated and, therefore, normally takes place over a temperature range above room temperature, preferably between 40 and 200° C., more preferably between 60 and 180° C. and with a particular preference for between 80 and 160° C.

The reaction in accordance with the invention normally proceeds for between 10 minutes and up to 48 hours, preferably between 1 hour and 6 hours.

Optionally, to homogenise the reaction mixture, inert ground material, for example, metal-, glass-, ceramic cones or Raschig or Pall rings can be added.

The procedure in accordance with the invention is best suited to the representation of defined compounds, however, without being limited to them. If suitable products are used, such as, e.g. diamines or di-haloarylenes it may also be employed for the synthesis of oligomeric or polymeric compounds. The procedure in accordance with the invention displays the following surprising advantages:

- When the halo-, dihalo-, alkyloxy-, aryloxy-, dialkyloxy- or dialkyloxy-phosphines employed are exposed to the air they do not exhibit any pyrophoric behaviour; depending upon their organic residue, they are partially stable to atmospheric oxygen and water. This is a particular advantage for industrial use in explosion-protected zones, compared to procedures of prior art.
- To some extent, the halo-, dihalo-, alkoxy-, aryloxy, dialkyloxy-, or dialkoxy-phosphines employed can be prepared economically with simple procedures known from the literature or they are to some extent commercially available.
- As a result of the high reaction completion rates, high yields of raw products are obtained.
- As a consequence of the very small proportion of by-products and especially of the very small content of regio-isomers which are very difficult to separate out by distillation and/or crystallisation, the yield of products having a purity of >99.5% or of even more pure products with a purity of >99.9% is clearly greater than the results obtained using the procedures of prior art. (see Table 1, in the Experimental Results part of this application).

The levels of purity achieved by the procedure described here can only be obtained—if at all—from previously-described procedures by expensive purification operations and, consequently, compounds obtained with a purity of more than 99.5% by the procedure described here form a constituent part of this invention.

Equally, compounds obtained by the procedure described here are characterised in that the proportional part in % (determined by ¹H-NMR and/or HPLC) of possible regio-isomers which can be formed during the C—N-coupling amount to less than 1% with respect to the desired isomers form a constituent part of this invention.

The described invention is explained by the following examples but is by no means limited to these examples—rather the technical expert can apply the principle involved in a simple and natural manner to the systems described above or to be found in the literature referred to.

Synthesis of the Arylamines

The following syntheses were carried out under a dry pure-nitrogen or argon atmosphere using dry solvents. The products used [sodium-tert-butanolate, palladium (II)acetate, chloro-di-tert-butylphosphine, diphenylamine 1-naphthyl-phenylamine, bis(4-methoxyphenyl) amine] were obtained from ALDRICH and used without further purification. The 2,2',7,7'-tetrabrom-9,9;spirobifluorene (purity>99.7%) was obtained according to the method of R. Wu, J. S. Schumm, D. L. Pearson, J. M. Tour, J. Org. Chem., 1996, 61, 6906–6921 and appropriate purification by recrystallisation from dioxane. The structural integrity of the products was determined by ¹H-NMR-spectroscopy and the purity of the products by HPLC.

EXAMPLE 1

2,2',7,7'-tetrakis-(N,N'-diphenylamino)spiro-9,9'-bifluorene

A degassed suspension of 31.6 g (50 mmol) of 2,2',7,7'-tetrabromo-9,9'spirobifluorene and 30.3 (315 mmol)) of sodium-tert-butanolate were added to 400 ml of toluol with 361 mg=380 µl (2 mmol) of chloro-di-tert-butylphosphine. After stirring for 5 minutes 225 mg (1 mmol) palladium(II) acetate and then 38.1 g (225 mmol)) of diphehylamine were added to the reaction mixture. The reaction mixture was heated under reflux for 2 hours. After cooling to 60° C. 500 ml of water were added, and stirring continued for 1 hour. The precipitated product was filtered off, washed with water and dried to constant weight in a vacuum at 80° C. A second product fraction was obtained by concentrating the organic phase to 100 ml and filtering off the resulting precipitate. The combined product fractions were recrystallised from dioxane (2.2 ml/1 g) with the addition of a little hydrazine hydrate until the desired degree of purity was obtained after which the material was sublimated under a high vacuum (p=5×10⁻⁵ mbar, T=375° C.) (see Table 1).

¹H-NMR (0.8 ml CDCl₃ with 30 µl hydrazine hydrate): 7.44 (d, ³$J_{HH}$=8.2 Hz, H4, 4H), 7.20–7.16 (m, 16H), 6.99–6.95 (m, 24 H), 6.91 (dd ³JHH=8.2 Hz, ⁴$J_{HH}$=2.0 Hz, H3, 4lH), 6.68 (d,⁴$J_{HH}$=2.0 Hz, H1, 4H).

EXAMPLE 2

Carried out in a manner analogous to that of Example 1 with the difference that the 2,2',7,7'-tetrabromo-9,9'-spirofluorene and the diphenylamine are added first and the sodium-tert-butanolate is added afterwards. For yield/level of purity see Table 1.

¹H-NMR: see Example 1

EXAMPLE 3

Comparison Example with Respect to Example 1 in Accordance with EP-A-802 173

Carried out in a manner analogous that of Example 1 with the difference that the chloro-di-tert-butylphosphine is replaced by 405 mg (2 mmol) of tri-tert-butylphosphine. For yield/level of purity see Table 1.

$^1$H-NMR: see Table 1

EXAMPLE 4

Comparison Example with Respect to Example 1 in Accordance with WO 01/40147

Carried out in a manner analogous to that of Example 1 with the difference that as the phosphine, di-tert-butylphosphineoxide is used and this is obtained by the hydrolysis of 361 mg=380 μl (2 mmol) of chloro-di-tert-butylphosphine as described under "Experiment 2 in accordance with WO 01/40147". Because of the slow reaction speed the reaction mixture was heated under reflux for 24 hours. Even after this period of time full conversion of the 2,2',7,7'-tetra-bromo-9,9'-spirobifluorene was not achieved, see Table 1.

EXAMPLE 5

2,2',7,7'-tetrakis-(N-phenyl-N'-(1-naphthyl)amino-spiro-9,9'-bifluorene

A degassed suspension of 31.6 g (50 mmol) of 2,2',7,7'-tetrabromo-9,9'spirobifluorene and 30.3 (315 mmol)) of sodium-tert-butanolate were reacted in 400 ml of toluol with 361 mg=380 μl (2 mmol) of chloro-di-tert-butylphosphine. After stirring for 5 minutes 225 mg (1 mmol) palladium(II) acetate and then 49.3 g (225 mmol)) of 1-naphthyl-phenylamine was added to the reaction mixture. The reaction mixture was heated under reflux for 2 hours. After cooling to 60° C. 500 ml of water were added and stirring continued for 1 hour. The organic phase was separated off and concentrated to dryness. The residue was taken up in 500 ml of dichloromethane and slowly added with stirring to 1,000 ml of methanol. The product obtained in this way was separated by suction, washed with methanol, dried, recrystallised from dioxane (2.0 ml/1 g) with the addition of a little hydrazine hydrate until the desired degree of purity was obtained after which the material was sublimated under high vacuum (p=5×10$^{-5}$ mbar, T=405° C.). For yield/purity see Table 1.

$^1$H-NMR (0.8 ml CDCl$_3$ with 30 μl hydrazine hydrate): 7.88–7.84 (m, 8H) 7.75–7.73 (m, 4H), 7.46–7.41 (m, 8 H), 7.34–7.26 (m, 8 H) 7.22–7.20 (m, 4H), 7.12–7.08 m, 8H), 6.86–6.80 (m, 16 H), 6.77–6.74 (m, 4H).

EXAMPLE 6

Comparison Example with Respect to Example 5 in Accordance with EP-A-0 802 173

Carried out in a manner analogous to that of Example 4 with the difference that the chloro-di-tert-butylphosphine was replaced by 405 mg (2 mmol) of tri-tert-butylphosphine. For yield and purity see Table 1.

EXAMPLE 7

2,2',7,7'-tetrakis-(N,N'-di(4-methoxy)phenylaminespiro-9,9'-bifluorene

A degassed suspension of 31.6 g (50 mmol) of 2,2',7,7'-tetrabromo-9,9'spirobifluorene and 30.3 (315 mmol)) of sodium-tert-butanolate were added to 400 ml of toluol with 361 mg=380 μl (2 mmol) of chloro-di-tert-butylphosphine. After stirring for 5 minutes 225 mg (1 mmol) palladium(II) acetate and then 51.6 g (225 mmol)) of bis(4-methoxyphenylamine) was added to the reaction mixture. The reaction mixture was heated under reflux for 2 hours. After cooling to 60° C. 500 ml of water were added and stirring continued for 1 hour. The organic phase was filtered off and concentrated to dryness. The residue was taken up in 500 ml of dichloromethane and slowly added to 1,000 ml of methanol with stirring. The product obtained in this way was separated by suction, washed with methanol, dried, recrystallised from dioxane (1.6 g/1 ml) with the addition of hydrazine hydrate until the desired level of purity was obtained and subsequently dried below the melting point under a high vacuum. For yield and purity, see Table 1

$^1$H-NMR (0.8 ml CDCl$_3$ with 30 μl hydrazine hydrate): 7.35 (d, $^3J_{HH}$=10.4 Hz, H4, 4H), 6.92–6.89 (m, 16H), 6.79(dd, $^3J_{HH}$=10.4 Hz, $^4J_{HH}$=2.5 Hz, H3, 4lH), 6.77–6.73 (m, 16 H), 6.54(d, $^4J_{HH}$=2.5 Hz, H1, 4H), 3.69 (s, CH$_3$, 24H).

EXAMPLE 8

Comparison Example with Respect to Example 7 in Accordance with EP-A-0 802 173

Carried out in a manner analogous to that of Example 6 with the difference that the chloro-di-tert-butylphosphine was replaced by 405 mg (2 mmol) of tri-tert-butylphosphine. For yield and purity see Table 1.

EXAMPLE 9

Synthesis of 4,4'-bis(4-tert-butylphenylphenylamino)biphenyl 2 l of xylol were degassed under nitrogen in a 4 l nitrogen flask. To this was added 86.5 g (0.90 mol) of sodium-tert-butanolate after which 85.0 ml (0.45 mol) of chloro-di-tert-butylphosphine were added over a period of 5 minutes with effective stirring. 10.0 kg (29.7 mol) of N,N'-diphenyl benzidine in 170 l of xylol were placed in a 500 l vessel with an anchor stirrer. While effective stirring was maintained the flask was evacuated three times to an internal pressure of about 50 mbar and then flooded with dry nitrogen (99.998%). To the solution rendered inert in this manner was added 8.7 kg (90.5 mol) of solid sodium-tert-butanolate and the contents of the flask stirred for 30 minutes at room temperature. Then, the mixture of chloro-tert-butylphosphine and sodium-tert-butanolate in 2 l of xylol was added and the whole stirred for 15 minutes. Then 33.5 g (0.15 mol) of palladium (II)acetate was added, this being followed by 15 minutes stirring. Finally, 13.9 kg (65.2 mol) of 1-bromo-4-tert-butylbenzol were added. The reaction mixture was heated, with effective stirring, for three hours under reflux. After cooling to 60° C., 75 l of deionised water were added and stirring continued for at least a further 3 hours. The precipitated solid material sucked out by means of a pressure filter and then stirred three times with 75 l lots of deionised water and twice with 75 l lots of ethanol. After drying with nitrogen the filter cake was dried under reduced pressure in a drying cupboard.

Yield: 11.0 kg (18.3 mol), 61.6 of theory Purity: 99.8% (HPLC), regio-isomers <0.1% (HPLC)

TABLE 1

Yields and composition of the products obtained from Examples 1–8

| Example | Yield of raw product | Purity of raw product | Regio-isomer 1 | Regio-isomer 2 | Number of recrystalisation steps | Final yield; purity |
|---|---|---|---|---|---|---|
| 1 | 48.2 g = 97.7% | 98.81% | 0.26% | 0.09% | 3 | 83.4%; >99.9% |

TABLE 1-continued

Yields and composition of the products obtained from Examples 1–8

| Example | Yield of raw product | Purity of raw product | Regio-isomer 1 | Regio-isomer 2 | Number of recrystalisation steps | Final yield; purity |
|---|---|---|---|---|---|---|
| 2 | 47.9 g = 97.3% | 98.64% | 0.27% | 0.09% | 4 | 79.8%; >99.9% |
| 3 | 45.8 g = 93.1% | 96.44% | 0.71% | 0.25% | 9 | 67.3%; >99.9% |
| 4 | Reaction mixture contained about 56% of the product. Processing was discontinued | | | | | |
| 5 | 56.4 g = 95.2% | 95.97% | 0.86% | 0.33% | 3 | 84.1%; >99.5% |
| 6 | 52.2 g = 88.0% | 96.31% | 1.58% | 0.49% | 7 | 57.9%; >99.5% |
| 7 | 57.9 g = 94.6% | 98.06% | 0.385 | 0.08% | 2 | 76.3%; >99.9% |
| 8 | 48.3 g = 83.5% | 97.10% | 1.19% | 0.29% | 5 | 51.9%; >99.9% |

The invention claimed is:

1. A method of preparing tertiary amines having formula (I)

$$Ar-(NR1R2)_n \quad (I),$$

the method comprising:
reacting secondary amines having formula (II)

$$H-NR1R2 \quad (II)$$

with aromatic amines or heteroaromatic amines of the formula (III)

$$(X)_n-Ar \quad (III)$$

in the presence of
a base,
a nickel or palladium compound, and
at least one phosphine selected from the group consisting of:
a monomeric halo-phosphine of the general formula Y—PR4R5,
an oligomeric halo-phosphine of the general formula Y—PR4R5,
a polymeric halo-phosphine of the general formula Y—PR4R5,
a dihalo-phosphine of the general formula (Y)$_2$PR4,
an alkoxy-phosphine of the general formula R3O—PR4R5,
an aryloxy-phosphine of the general formula R3O—PR4R5,
a dialkoxy-phosphine of the general formula (R3O)$_2$—PR4,
a diaryloxy-phosphine of the general formula (R3O)$_2$—PR4, and
mixtures thereof in an inert solvent;
wherein the residues and indices have the following meaning:
Ar are all:
aromatic groups with 6 to 40 carbon atoms or heteroaromatic groups with 2 to 40 carbon atoms, either of which can be unsubstituted or substituted by at least one linear, branched, or cyclic alkyl- or alkoxy residues having 1 to 20 carbon atoms, wherein one or more non-vicinal CH$_2$-groups of the alkyl- or alkoxy residues can be replaced by O, S, C=O, or a carboxy group; or by unsubstituted aryl- or hetero-aryl residue having 4 to 20 carbon atoms, fluorine or cyano- or nitro-groups;

R1 and R2 are individually the same or different and are:
a linear or branched mono-, bi-, tri-, or poly-cyclic aliphatic having 1 to 20 carbon atoms where the nitrogen can form a part of the ring system and where again one or more non-vicinal CH$_2$-groups can be substituted by NR4, O, S, C=O, or a carboxy-group, and aromatics with 6 to 40 carbon atoms or heteroaromatics with 2 to 40 carbon atoms, either of which can be unsubstituted or substituted by one or more linear, branched, or cyclic alkyl- or alkoxy residues having 1 to 20 carbon atoms where again one or more non-vicinal CH$_2$-groups can be replaced by O, S, C=O, or a carboxy group; or by unsubstituted aryl- or hetero-aryl residues having 4 to 20 carbon atoms, fluorine or cyano- or nitro-groups;

R3 is:
a linear or branched alkyl residue having 1 to 12 carbon atoms or an aryl residue having 6 to 12 carbon atoms;

R4 and R5 are individually the same or different and are:
a linear, branched or mono-, di- or tricyclic alkyl-residue having 1 to 12 carbon atoms, where again one or more non-vicinal CH$_2$-groups can be substituted by O, or an aryl or heteroaryl-residue having 4 to 12 carbon atoms which can be substituted by one or more linear, branched or cyclic alkyl- or alkoxy residues having 1 to 10 carbon atoms, where again one or more non-vicinal CH$_2$-groups can be substituted by O, S, C=O, or a carboxy group;

X is a suitable reactive leaving group,
Y is fluorine, chlorine or iodine, and
n is a whole number between 1 and 10.

2. The method of claim 1, characterized in that Ar is a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine.

3. The method of claim 1, characterized in that the alkyl-, aryl-, or heteroaryl residues of the R1 and R2 residues are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, a morpholino-residue, or a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine.

4. The method of claim 1, characterized in that the base is one of the inorganic bases selected from the group consisting of alkali- and alkaline earth metal carboxylates, alkali- and alkaline earth metal carbonates, hydrogen carbonate and hydrogen phosphate, sodium acetate, potassium acetate, sodium phosphate, potassium phosphate, and mixtures thereof.

5. The method of claim 1, characterized in that the base is one of the organic bases selected from the group consisting of metal alcoholates of the type MO—R3, wherein M is an electro-positive metal.

6. The method of claim 5, characterized in that the electro-positive metal M is lithium, sodium, potassium, magnesium, or zinc.

7. The method of claim 1, characterized in that the R3 residue is a methyl-, ethyl-, propyl-, iso-propyl-, butyl-, iso-butyl-, sec-butyl-, tert-butyl-, tert-pentyl-, tert-hexyl-or phenyl-alkyl or aryl residue.

8. The method of claim 1, characterized in that the base is a metal alcoholate organic base of the type MO—R3 and the R3 residue is a methyl-, an ethyl-, a propyl-, an iso-propyl-, a butyl-, an iso-butyl-, a sec-butyl-, a tert-butyl-, a tert-pentyl, a tert-hexyl-, or a phenyl-alkyl or aryl residue.

9. The method of claim 1, characterized in that the base is a metal alcoholate organic base of the type MO—R3 and the R3 residue is sodium-tert-butanolate.

10. The method of claim 1, characterized in that the alkyl-, aryl-, or heteroaryl residues of the R4 and R5 residues are a methyl-, an ethyl-, a propyl-, an iso-propyl-, a butyl-, an iso-butyl-, a sec-butyl-, a tert-butyl, a tert-pentyl-, a tert-hexyl-, a cyclopentyl-, a cyclohexyl-, a phenyl-, an o-tolyl-, a 2,6-dimethylphenyl-, a mesityl-, a 2-iso-propylphenyl-, a 2,6-di-iso-propylphenyl-, a 2-tert-butylphenyl-, a 2-methoxyphenyl-, a 2,6-dimethoxyphenyl-, a 2,4,6-trimethoxyphenyl-, or a 2-biphenyl-alkyl-, aryl- or heteroaryl residue.

11. The method of claim 10, characterized in that the R4 and R5 residues are tert-butyl residues.

12. The method of claim 1, characterized in that X is chlorine, bromine, iodine, methylsulphonate, tosylate, triflate, nonaflate, or a diazonium salt group.

13. The method of claim 1, characterized in that the nickel compound is a nickel-(II)-compound, a dispersed or colloidal metallic nickel, a supported or unsupported metallic nickel, or other nickel-(0)-compounds.

14. The method of claim 13, characterized in that the nickel compound is selected from the group consisting of a nickel-(II)-halogenide, a nickel-(II)-biscarboxylate, a nickel-(II)-ketonate, an olefinenickel-(II)-halogenide, an allylnickel-(II)-halogenide, and complexes derived from a nickel-(II)-halogenide, a nickel-(II)-biscarboxylate, or a nickel-(II)-ketonate.

15. The method of claim 1, characterized in that the palladium compound is a palladium-(II)-compound, a dispersed or colloidal metallic palladium, a supported or unsupported metallic palladium, and other palladium-(0)-compounds.

16. The method of claim 15, characterized in that the palladium compound is selected from the group consisting of a palladium-(II)-halogenide, a palladium-(II)-biscarboxylate, a palladium-(II)-ketonate, a nitrilepalladium-(II)-halogenide, an olefinepalladium-(II)-halogenide, an allylpalladium-(II)-halogenide, and simple complexes derived from a palladium-(II)-halogenide, a palladium-(II)-biscarboxylate, or a palladium-(II)-ketonate.

17. The method of claim 1, characterized in that the palladium compound is palladium-(II)-acetate or $Pd_2(dba)_3$.

18. The method of claim 1, characterized in that the inert solvent is selected from the group consisting of an aromatic solvent, toluene, an isomeric xylene, an ether, a cyclic ether, a polyether, di-iso-propylether, methyl-tert-butylether, di-n-butyl ether, anisole, tetrahydrofuran, dioxane, a di-, tri- and tetra ethyleneglycoldimethyl- or ethylether, an oligo- or polyethyleneglycoldimethyl- or ethylether, N,N-dialkylcarboxylicacidamide, a N-alkyllactone, dimethylformamide, dimethylacetamide, N-methylpyridine-2-one, and mixtures thereof.

19. The method of claim 1, characterized in that oligomeric or polymeric compounds are synthesized by the use of diamines or di-haloarylenes.

20. The method of claim 1, characterized in that

Ar is a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue; and the aryl- or heteroaryl residues of the R1 and R2 residues are a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine.

21. The method of claim 1, characterized in that

Ar is a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue;

the aryl- and heteroaryl residues of the R4 and R5 residues are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue.

22. The method of claim 1, characterized in that the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;

the aryl- or heteroaryl residues of the R1 and R2 residues are a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue; and the aryl- and heteroaryl residues of the R4 and R5 residues are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue.

23. The method of claim 1, characterized in that

Ar is a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the R4 and R5 residue are tert-butyl residues.

24. The method of claim 1, characterized in that the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;

the aryl- or heteroaryl residues of the R1 and R2 residues are a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the R4 and R5 residue are tert-butyl residues.

25. The method of claim 1, characterized in that

Ar is a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;

the aryl- or heteroaryl residues of the R1 and R2 residues are a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine;

the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue;

the aryl- and heteroaryl residues of the R4 and R5 residues are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue;

the base is selected from the group consisting of an sodium acetate, potassium acetate, sodium carbonate, potassium carbonate, sodium phosphate, potassium phosphate, and metal alcoholates of the type MO—R3, where M is lithium, sodium, potassium, magnesium, or zinc and R3 is a residue selected from the group consisting of a methyl-, an ethyl-, a propyl-, an iso-propyl-, a butyl-, an iso-butyl-, a sec-butyl-, a tert-butyl-, a tert-pentyl, a tert-hexyl-, or a phenyl-alkyl or aryl residue; and X is chlorine, bromine, iodine, methylsulphonate, tosylate, triflate, nonaflate, or a diazonium salt group.

* * * * *

UNITED STATES PATENT AND TRADEMARK OFFICE
CERTIFICATE OF CORRECTION

| | |
|---|---|
| PATENT NO. | : 7,250,519 B2 |
| APPLICATION NO. | : 10/494081 |
| DATED | : July 31, 2007 |
| INVENTOR(S) | : Philipp Stössel, Hubert Spreitzer and Heinrich Becker |

It is certified that error appears in the above-identified patent and that said Letters Patent is hereby corrected as shown below:

<u>Column 14</u>

Claim 1, line 3, delete "nitro-groups" and insert --nitro- groups--

Claim 1, line 5, delete "linear or branched" and insert --linear, branched or--

Claim 1, line 19, delete "nitro-groups" and insert --nitro- groups--

Claim 1, line 35, delete "chlorine or iodine" and insert --chlorine, bromine or iodine--

Claim 2, line 38, delete "benzol," and insert --benzene,--

Claim 3, line 44-52, delete "methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, a morpholino-residue, or a substituted or unsubstituted benzol, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine." and insert --methyl- residue, an ethyl- residue, a propyl- residue, an iso-propyl- residue, a butyl- residue, an iso-butyl- residue, a sec-butyl- residue, a tert-butyl- residue, a cyclopentyl- residue, a cyclohexyl- residue, a cycloheptyl- residue, a N-methylpiperazinyl- residue, a morpholino- residue, or a substituted or unsubstituted benzene, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine, or pyrazine.--

UNITED STATES PATENT AND TRADEMARK OFFICE
CERTIFICATE OF CORRECTION

PATENT NO. : 7,250,519 B2
APPLICATION NO. : 10/494081
DATED : July 31, 2007
INVENTOR(S) : Philipp Stössel, Hubert Spreitzer and Heinrich Becker It is certified that error appears in the above-identified patent and that said Letters Patent is hereby corrected as shown below:

Claim 4, line 57, delete "bonate and hydrogen phosphate," and insert --bonates and hydrogen phosphates,--

Column 15

Claim 7, line 3, delete "tert-hexyl-or" and insert --tert-hexyl- or--

Claim 9, lines 11-12, delete "a metal alcoholate organic base of the type MO-R3 and the R3 residue is"

Column 16

Claim 20, line 2, delete "benzol," and insert --benzene,--

Claim 20, lines 7-12, delete "the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue; and" and insert --the alkyl residues of the R1 and R2 residue are a methyl- residue, an ethyl- residue, a propyl- residue, an iso-propyl- residue, a butyl- residue, an iso-butyl- residue, a sec-butyl- residue, a tert-butyl- residue, a cyclopentyl- residue, a cyclohexyl- residue, a cycloheptyl- residue, a N-methylpiperazinyl- residue, or a morpholino- residue;--

Claim 20, line 15, delete "benzol," and insert --benzene,--

UNITED STATES PATENT AND TRADEMARK OFFICE
CERTIFICATE OF CORRECTION

PATENT NO.        : 7,250,519 B2
APPLICATION NO. : 10/494081
DATED             : July 31, 2007
INVENTOR(S)       : Philipp Stössel, Hubert Spreitzer and Heinrich Becker It is certified that error appears in the above-identified patent and that said Letters Patent is hereby corrected as shown below:

Claim 21, line 21, delete "benzol," and insert --benzene,--

Claim 21, lines 26-31, delete "the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue;" and insert --the alkyl residues of the R4 and R5 residue are a methyl- residue, an ethyl- residue, a propyl- residue, an iso-propyl- residue, a butyl- residue, an iso-butyl- residue, a sec-butyl- residue, a tert-butyl residue, a tert-pentyl- residue, a tert-hexyl- residue, a cyclopentyl- residue, or a cyclohexyl- residue;--

Claim 21, lines 33-38, delete "are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue." and insert --are a phenyl- residue, an o-tolyl- residue, a 2,6-dimethylphenyl- residue, a mesityl- residue, a 2-iso-propylphenyl- residue, a 2,6-di-iso-propylphenyl- residue, a 2-tert-butylphenyl- residue, a 2-methoxyphenyl- residue, a 2,6-dimethoxyphenyl- residue, a 2,4,6-trimethoxyphenyl- residue, or a 2-biphenyl- residue.--

UNITED STATES PATENT AND TRADEMARK OFFICE
CERTIFICATE OF CORRECTION

| | | |
|---|---|---|
| PATENT NO. | : 7,250,519 B2 | Page 4 of 7 |
| APPLICATION NO. | : 10/494081 | |
| DATED | : July 31, 2007 | |
| INVENTOR(S) | : Philipp Stössel, Hubert Spreitzer and Heinrich Becker | |

It is certified that error appears in the above-identified patent and that said Letters Patent is hereby corrected as shown below:

Claim 22, lines 40-45, delete "the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;" and insert --the alkyl residues of the R1 and R2 residue are a methyl- residue, an ethyl- residue, a propyl- residue, an iso-propyl- residue, a butyl- residue, an iso-butyl- residue, a sec-butyl- residue, a tert-butyl- residue, a cyclopentyl- residue, a cyclohexyl- residue, a cycloheptyl- residue, a N-methylpiperazinyl- residue, or a morpholino- residue;--

Claim 22, line 47, delete "benzol," and insert --benzene,--

Claim 22, lines 52-57, delete "the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue; and" and insert --the alkyl residues of the R4 and R5 residue are a methyl- residue, an ethyl- residue, a propyl- residue, an iso-propyl- residue, a butyl- residue, an iso-butyl- residue, a sec-butyl- residue, a tert-butyl residue, a tert-pentyl- residue, a tert-hexyl- residue, a cyclopentyl- residue, or a cyclohexyl- residue; and--

UNITED STATES PATENT AND TRADEMARK OFFICE
CERTIFICATE OF CORRECTION

PATENT NO.      : 7,250,519 B2
APPLICATION NO. : 10/494081
DATED           : July 31, 2007
INVENTOR(S)     : Philipp Stössel, Hubert Spreitzer and Heinrich Becker It is certified that error appears in the above-identified patent and that said Letters Patent is hereby corrected as shown below:

Claim 22, lines 59-64, delete "are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue." and insert --are a phenyl- residue, an o-tolyl- residue, a 2,6-dimethylphenyl- residue, a mesityl- residue, a 2-iso-propylphenyl- residue, a 2,6-di-iso-propylphenyl- residue, a 2-tert-butylphenyl- residue, a 2-methoxyphenyl- residue, a 2,6-dimethoxyphenyl- residue, a 2,4,6-trimethoxyphenyl- residue, or a 2-biphenyl- residue.--

Claim 23, line 66, delete "benzol," and insert --benzene,--

Column 17
Claim 24, lines 6-11, delete "the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;" and insert --the alkyl residues of the R1 and R2 residue are a methyl- residue, an ethyl- residue, a propyl- residue, an iso-propyl- residue, a butyl- residue, an iso-butyl- residue, a sec-butyl- residue, a tert-butyl- residue, a cyclopentyl- residue, a cyclohexyl- residue, a cycloheptyl- residue, a N-methylpiperazinyl- residue, or a morpholino- residue;--

UNITED STATES PATENT AND TRADEMARK OFFICE
CERTIFICATE OF CORRECTION

| | |
|---|---|
| PATENT NO. | : 7,250,519 B2 |
| APPLICATION NO. | : 10/494081 |
| DATED | : July 31, 2007 |
| INVENTOR(S) | : Philipp Stössel, Hubert Spreitzer and Heinrich Becker |

It is certified that error appears in the above-identified patent and that said Letters Patent is hereby corrected as shown below:

Claim 24, line 13, delete "benzol," and insert --benzene,--

Claim 25, lines 25-30, delete "the alkyl residues of the R1 and R2 residue are a methyl-residue, an ethyl-residue, a propyl-residue, an iso-propyl-residue, a butyl-residue, an iso-butyl-residue, a sec-butyl-residue, a tert-butyl-residue, a cyclopentyl-residue, a cyclohexyl-residue, a cycloheptyl-residue, a N-methylpiperazinyl-residue, or a morpholino-residue;" and insert --the alkyl residues of the R1 and R2 residue are a methyl- residue, an ethyl- residue, a propyl- residue, an iso-propyl- residue, a butyl- residue, an iso-butyl- residue, a sec-butyl- residue, a tert-butyl- residue, a cyclopentyl- residue, a cyclohexyl- residue, a cycloheptyl- residue, a N-methylpiperazinyl- residue, or a morpholino- residue;--

Claim 25, line 32, delete "benzol," and insert --benzene,--

<u>Column 18</u>
Claim 25, lines 5-10, delete "the alkyl residues of the R4 and R5 residue are a methyl-residue, an ethyl-residue, a propyl-residue, an iso-propyl-residue, a butyl-residue, an iso-butyl-residue, a sec-butyl-residue, a tert-butyl residue, a tert-pentyl-residue, a tert-hexyl-residue, a cyclopentyl-residue, or a cyclohexyl-residue;" and insert --the alkyl residues of the R4 and R5 residue are a methyl- residue, an ethyl- residue, a propyl- residue, an iso-propyl- residue, a butyl- residue, an iso-butyl- residue, a sec-butyl- residue, a tert-butyl residue, a tert-pentyl- residue, a tert-hexyl- residue, a cyclopentyl- residue, or a cyclohexyl- residue;--

UNITED STATES PATENT AND TRADEMARK OFFICE
CERTIFICATE OF CORRECTION

PATENT NO. : 7,250,519 B2
APPLICATION NO. : 10/494081
DATED : July 31, 2007
INVENTOR(S) : Philipp Stössel, Hubert Spreitzer and Heinrich Becker It is certified that error appears in the above-identified patent and that said Letters Patent is hereby corrected as shown below:

Claim 25, lines 12-17, delete "are a phenyl-residue, an o-tolyl-residue, a 2,6-dimethylphenyl-residue, a mesityl-residue, a 2-iso-propylphenyl-residue, a 2,6-di-iso-propylphenyl-residue, a 2-tert-butylphenyl-residue, a 2-methoxyphenyl-residue, a 2,6-dimethoxyphenyl-residue, a 2,4,6-trimethoxyphenyl-residue, or a 2-biphenyl-residue;" and insert --are a phenyl- residue, an o-tolyl- residue, a 2,6-dimethylphenyl- residue, a mesityl- residue, a 2-iso-propylphenyl- residue, a 2,6-di-iso-propylphenyl- residue, a 2-tert-butylphenyl- residue, a 2-methoxyphenyl- residue, a 2,6-dimethoxyphenyl- residue, a 2,4,6-trimethoxyphenyl- residue, or a 2-biphenyl- residue;--

Signed and Sealed this

Tenth Day of November, 2009

David J. Kappos
*Director of the United States Patent and Trademark Office*